US00PP26087P3

(12) United States Plant Patent
Grosser

(10) Patent No.: US PP26,087 P3
(45) Date of Patent: Nov. 17, 2015

(54) SWEET ORANGE TREE NAMED 'OLL-8'

(50) Latin Name: *Citrus sinensis*
Varietal Denomination: OLL-8

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 190 days.

(21) Appl. No.: 13/987,609

(22) Filed: Aug. 13, 2013

(65) Prior Publication Data

US 2015/0052645 P1 Feb. 19, 2015

(51) Int. Cl.
*A01H 5/08* (2006.01)

(52) U.S. Cl.
USPC ..... Plt./202
CPC ..... *A01H 5/0806* (2013.01)

(58) Field of Classification Search
USPC ..... Plt./202, 201
See application file for complete search history.

(56) References Cited

U.S. PATENT DOCUMENTS

| | | | |
|---|---|---|---|
| PP21,224 | P2 | 8/2010 | Grosser et al. |
| PP21,356 | P3 | 10/2010 | Gmitter, Jr. et al. |
| PP21,535 | P2 | 11/2010 | Grosser et al. |
| 2013/0276180 | P1 | 10/2013 | Grosser |

OTHER PUBLICATIONS

Citrus. UF University of Florida IFAS Apr. 2013, 2 pp.*
U.S. Appl. No. 14/121,859, filed Oct. 27, 2014, Grosser.
U.S. Appl. No. 13/987,563, filed Aug. 7, 2013, Grosser.
Grosser et al., "Highlights from the UF/IFAS/CREC Citrus Improvement Program," presentation at the Florida Citrus Show, Ft. Pierce, Florida, Jan. 19-20, 2011.

* cited by examiner

*Primary Examiner* — June Hwu
(74) *Attorney, Agent, or Firm* — Dentons US LLP

(57) ABSTRACT

A new and distinct sweet orange clone 'OLL-8' has been developed from an unstable sweet orange selection, designated as 'OLL', using tissue culture techniques. Undeveloped ovules from fruit of selection 'OLL' were cultured in vitro to generate an embryogenic callus, from which multiple independent clones were regenerated via somatic embryogenesis. Regenerated plantlets (somaclones) were grafted to Swingle citrumelo rootstock and grown in the field for evaluation. Sweet orange clone 'OLL-8' was the most precocious bearing clone among the somaclone population, and thus the first to be selected for release, based on its stable propagation and outstanding qualities. 'OLL-8' produces high yields of high quality fruit, with exceptional flavor and juice color. It is expected to make a significant contribution to the sweet orange portfolio available to the not-from-concentrate juice producers in Florida and around the world.

4 Drawing Sheets

Latin name of the genus and species of the plant claimed: *Citrus sinensis*.

Variety denomination: 'OLL-8'.

BACKGROUND OF THE INVENTION

The present invention relates to a new and distinct variety of sweet orange tree named 'OLL-8'. 'OLL-8' is a somaclone regenerated from embryogenic callus (tissue culture) of 'Orie Lee Late' ('OLL') sweet orange (unpatented), with high-quality fruit that usually matures in the standard 'Valencia' (unpatented) time period. 'OLL' is believed to be an irradiation-induced mutant line originating from Pineapple sweet orange in an abandoned USDA trial attempting to generate a seedless Pineapple orange. 'OLL' attracted attention because it never dropped fruit, a serious problem with Pineapple, and held quality late into the summer. Propagations of 'OLL' were not uniform and included some trees of poor growth and productivity, as well as robust high-yielding trees. In efforts to generate genetically stable clones from the 'OLL' selection, tissue cultures (embryogenic callus) were established for the creation of somaclones. 'OLL-8' was the most precocious bearing tree among the population of somaclones regenerated. Trueness-to-type of 'OLL-8' was demonstrated by topworking two trees to Swingle citrumelo rootstock in CREC Block 18-North 40. Topworked trees are stable and productive, producing true-to-type fruit (for 4 consecutive years). In addition, young trees propagated on various rootstocks are stable and produce true-to-type fruit at multiple trial locations. 'OLL-8' was first asexually reproduced in Lake Alfred, Polk County, Fla., by topworking. The first asexually reproduced trees were originally Duncan grapefruit on Swingle citrumelo rootstock, topworked with 'OLL-8'. Since this time, hundreds of trees have been asexually propagated on multiple rootstocks using standard nursery practices. All asexually reproduced trees have been true-to-type to date.

SUMMARY OF THE INVENTION

Sweet orange selection 'OLL-8' produces round oranges with internal and external color significantly higher than that of standard 'Valencia' and often exceeds that of 'Rhode Red Valencia' (Table 1). Fruit holds on the tree exceptionally well, and maintains quality into the summer. 'OLL' seedling trees (including 'OLL-8') have shown good drought tolerance in the greenhouse, as overgrown trees in small pots rarely wilt, compared to other sweet orange seedlings, and 'OLL' somaclone field trees in general have shown better cold-tolerance in the previous two freezes than 'Valencia' trees in the same trial block. This apparent improved stress tolerance may be useful in the fight against Huanglongbing disease. Although minimal formal yield data is available, trees of 'OLL-8' appear to yield better than standard 'Valencia'. The original 'OLL-8' tree yielded more than five 90-lb boxes of fruit in 2012 (8-year old tree). Sensory (taste panel) analyses have repeatedly indicated that 'OLL-8' has a favorable 'Valencia'-like flavor profile. Therefore, 'OLL-8' has potential to improve the not-from-concentrate (NFC) portfolios of citrus juice processors. 'OLL-8' fruit generally has high juice content and produces a good number of pounds of solids. 'OLL-8' peels easier than a standard 'Valencia', but still requires quadrant scoring for clean peeling when grown under Florida conditions. With its added color, 'OLL-8' could also be a valuable addition to the Florida fresh market portfolio.

'OLL-8' is nearly identical in morphology to the original 'OLL' tree, and fruit of 'OLL-8' cannot be distinguished from the fruit of the original 'OLL' tree. However, the 'OLL-8' tree itself represents a significant improvement over the 'OLL' parent tree, since it has beneficial traits that can be stably propagated, whereas 'OLL' cannot be stably propagated. Parent tree 'OLL' is a single tree (i.e., not a commercial variety) of which more than 50% of propagations using standard budwood did not grow off properly, resulting in trees of inferior horticultural quality with poor health, vigor, and productivity. 'OLL-8' is a somaclone produced from 'OLL', which has proven to be stable during standard budwood propagation, with all propagated trees exhibiting normal health and vigor.

Table 1. Color Score Comparisons of 'OLL-8' with Selected Varieties. A color score of 36 is required for grade A orange juice, with higher color scores indicating darker orange color.

| | May, 2008 | June, 2008 | April, 2012 |
|---|---|---|---|
| 'Valencia' | 37.31 | 39.90 | 37.47 |
| 'Rhode Red Valencia' | 38.21 | 40.60 | 38.60 |
| 'OLL-8' | 40.52 | 41.80 | 39.62 |

BRIEF DESCRIPTION OF THE DRAWINGS

'OLL-8' is illustrated by the accompanying photographs, which show the tree's form, foliage and fruit. The colors shown are as true as can be reasonably obtained by conventional photographic procedures. The colors (except those in common terms) are described from R.H.S. Colour Chart published by The Royal Horticultural Society in London (2007, 5th Edition), in association with the Flower Council of Holland. The following photographs are of seven-year-old trees.

DETAILED BOTANICAL DESCRIPTION

Phenotypic Description of *Citrus sinensis* 'OLL-8'

Figure 1:
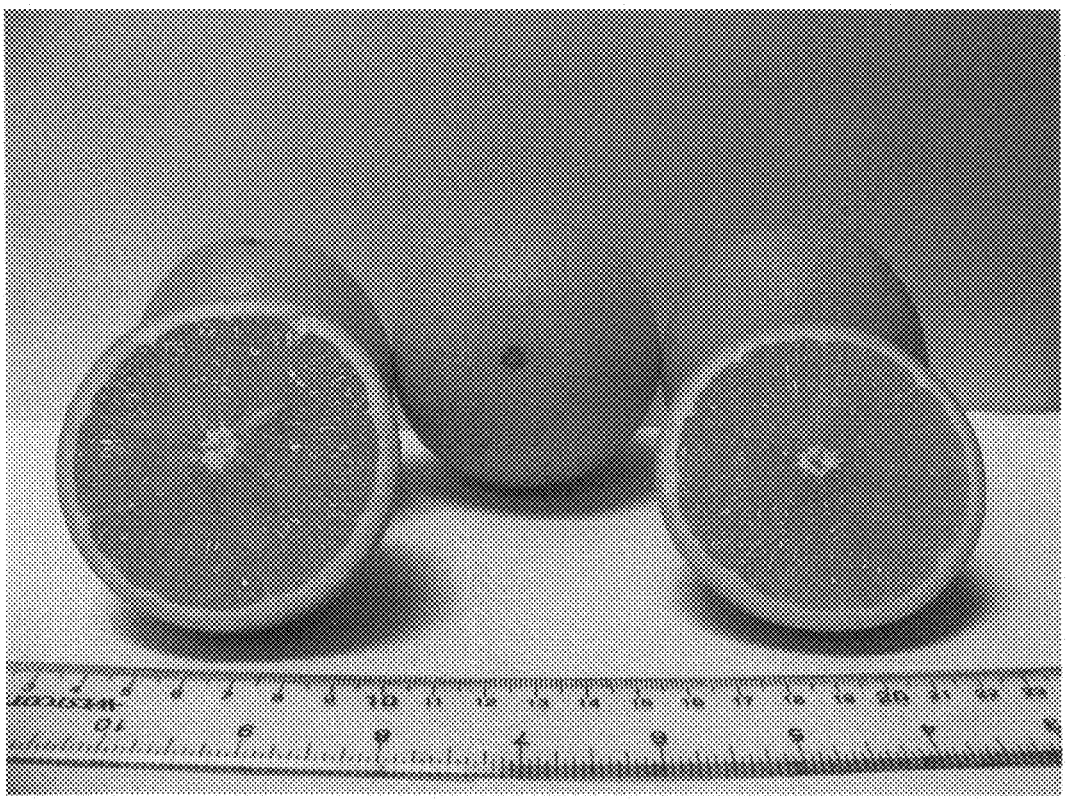
FIG. 1—Shows a close-up of the mature fruit with the rind present and cross-sectional view of the fruit when cut in the center (February, 2011).
Figure 2:
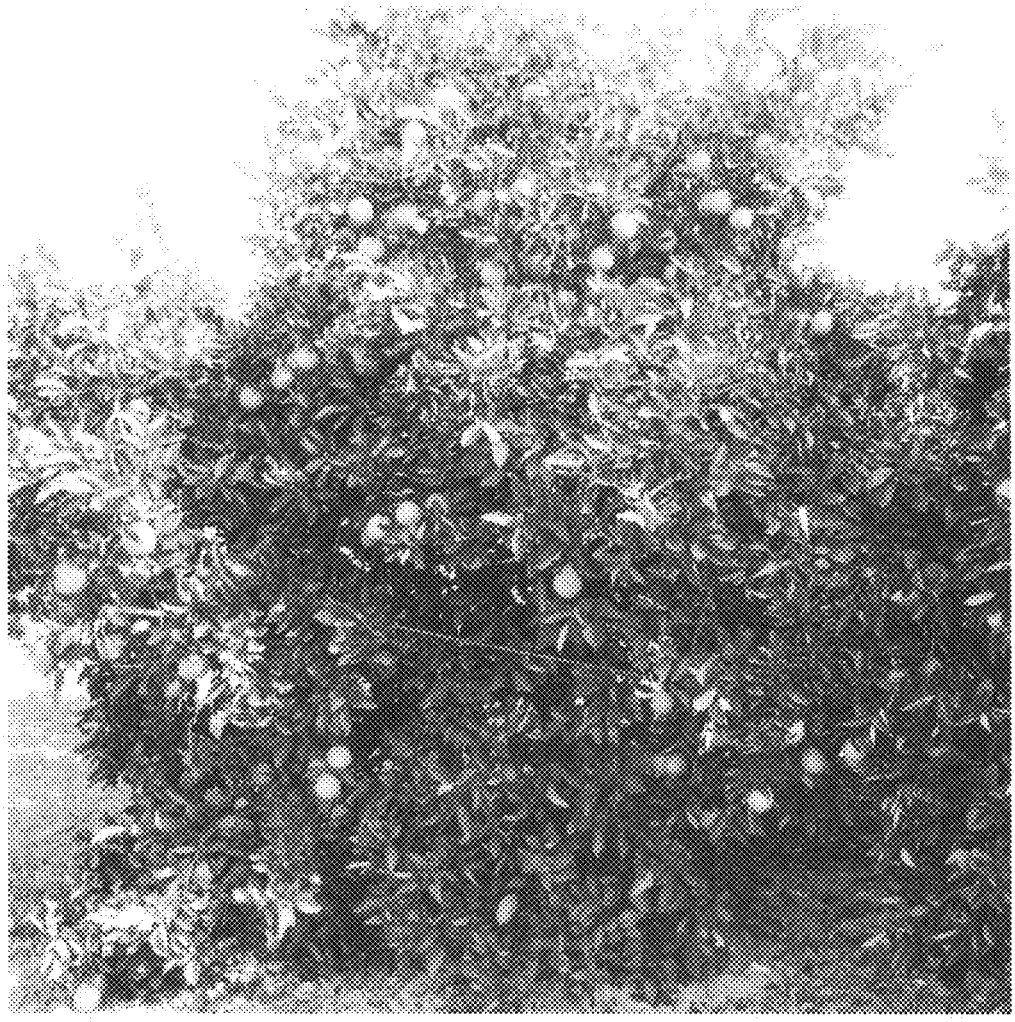
FIG. 2—Shows the original 'OLL-8' tree on Swingle citrumelo rootstock, planted East of St. Cloud, Fla. (February, 2011).
Figure 3:
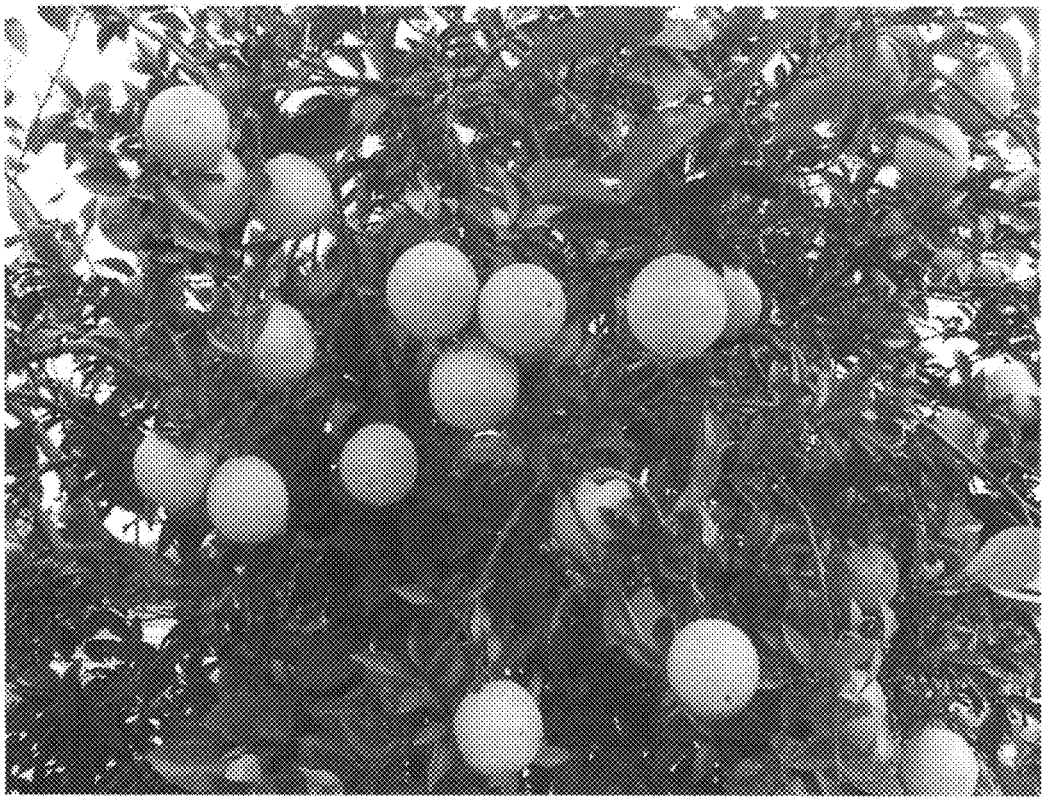
FIG. 3—Shows a top-worked tree of 'OLL-8' onto Swingle citrumelo in Lake Alfred, Fla. (February, 2011).
Figure 4:
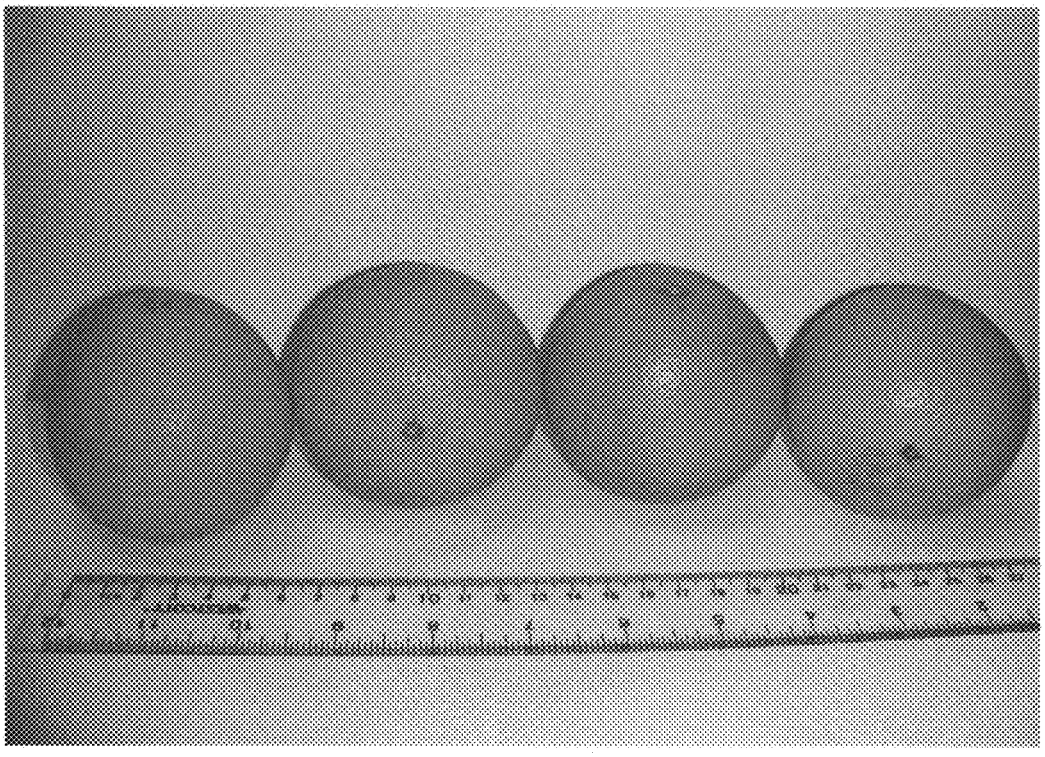
FIG. 4—Shows a close-up view of 'OLL-8' sweet orange fruit (February, 2011).

Classification:

Botanical: Citrus sinensis

Common name: Sweet orange

Parentage: 'OLL' ('Orie Lee Late') sweet orange tree, believed to have originated from a 40+ year old abandoned USDA irradiated Pineapple sweet orange trial.

Tree:

*Ploidy*.—Diploid.

*Size*.—Medium.

*Tree height*.—3.4 to 3.6 m.

*Tree spread*.—3 to 3.2 m.

*Vigor*.—Vigorous.

*Density*.—Canopies are quite dense.

*Form*.—The shape of the tree is obloid with upright and lateral branches growing, but tending toward medium angles after fruit has commenced.

*Growth habit* (*current season*).—Drooping.

Trunk:

*Trunk diameter*.—10 to 11 cm at 30 cm height above the ground.

*Trunk texture*.—Smooth.

*Trunk bark color*.—RHS 197A (greyed-green), irregularly striated with RHS N200A (brown).

Branches:

*Branch length*.—2.8 to 3 m from first crotch to the tip of leaf branch.

*Branch texture*.—Relatively smooth with small thorns or spines.

*Spine size*.—On mature branches, average 25 to 50 mm in length, and 2 to 5 mm in diameter at the base.

*Spine color*.—RHS 138A (green), with RHS 197A (greyed-green) at spine tip. Branch color (shoots from previous flush, hardened, and 4 to 5 mm in diameter): RHS 138A (green).

Leaves:

*Size* (*lamina average*).—Length: 105 mm. Width: 48 mm.

*L/W ratio*.—2.1 to 2.2.

*Thickness*.—Regular and average for commercial mandarin hybrids.

*Type*.—Simple.

*Shape*.—Elliptical.

*Apex*.—Slightly retuse.

*Base*.—Acute to sub-obtuse.

*Margin*.—Entire, slightly undulate.

*Surface*.—Upper surface: Glabrous. Lower surface: Medium veins that are pinnately netted.

*Color*.—Upper surface (adaxial): RHS 137A (green). Lower surface (abaxial): RHS 137C (green).

*Petiole*.—Shape: Brevipetiolate (shorter than leaf lamina); junction between petiole and lamina is articulate. Width (petiole wing): Narrow. Shape (petiole wing): Obovate. Color (petiole wing): RHS 137A (green). Length: 13 to 15 mm. Width: 2.8 to 3.5 mm. Color: RHS 137A (green).

Flowers and flower buds:

*Type*.—Hermaphrodite.

*Flower bearing* (*single or cluster*).—Flowers grown from leaf terminals and leaf axillaries. Some branches have flowers grown in clusters, each cluster consisting of 2 to 6 flowers.

*Diameter*.—Fully open flower with diameter ranging from 30 to 32 mm.

*Depth*.—Typical flower depth, between 19.5 to 20 mm.

*Blooming period*.—First bloom: Observed around mid to late March. Full bloom: Observed in early April of 2010.

*Flower bud size*.—Length: 2.0 mm for the initial visible flower bud; 18.7 mm for mature flower bud before fully open. Diameter: 2.2 mm for the initial visible flower bud; 5.5 to 6 mm for mature flower bud before fully open.

*Flower bud shape*.—Round dome shaped for initial visible flower bud; mature flower bud with elongated olive shape.

*Color*.—RHS 144D (yellow-green) for initial visible flower bud.

*Fertility*.—Self-fertile.

*Flower petals*.—Number: 5. Length: 21.0 to 22.0 mm on average. Width: 8.0 mm on average. Shape: Flat spatula shaped. Apex shape: Smooth acute shaped. Base shape: Even obtuse.

*Color*.—Upper surface: RHS 155D (white) to RHS 155C (white). Lower surface: RHS NN155A (white) with RHS 150D (yellow-green) spots distributed toward the petal apex. Margin: Smooth.

*Sepal*.—Number (per flower): 3 to 5 per flower. Shape: Short flat delta with acute angle at apex. Length: 2.8 mm. Width: 1.8 to 3.6 mm. Apex shape: Acute angle at apex. Margin: Smooth.

*Color*.—Upper surface: RHS 157B (green-white). Lower surface: RHS 157B (green-white).

*Pedicel*.—Number: 5. Length: 7 to 7.8 mm. Diameter: 0.8 to 1.0 mm. Color: RHS 144D (yellow-green).

*Stamen*.—Length: 13 to 14.8 mm. Pollen color (general): RHS 17A (yellow).

*Anther*.—Length: 3.0 to 3.2 mm. Width: 1.0 mm. Color: RHS 13B (yellow).

*Pistil*.—Number: 1. Length: 12.2 mm.

*Style length*.—8.9 mm.

*Style diameter*.—0.8 to 1 mm.

*Style color*.—RHS 144D (yellow-green).

*Ovary shape*.—Oval shaped.

*Ovary diameter*.—2.6 mm.

*Ovary color*.—RHS NN144D (yellow-green).

*Blossom period*.—In late March to early April in Central Florida.

*Fragrance*.—Fragrant.

Fruit:

*Fruit weight*.—180 to 205 g on average.

*Size*.—Uniform.

*Diameter*.—74.4 mm on average.

*Length*.—73.6 mm on average.

*Shape*.—Round and earth-shaped.

*Shape* (*cross-section*).—Round.

*Apex*.—Truncated with shallow dent mark.

*Base*.—No neck, with slightly rough peel surface.

Skin:

*Adherence*.—Albedo (mesocarp) to fresh (endocarp) is strong and relatively difficult to separate.

*Thickness*.—3 to 4 mm, thin to medium compared to other commercial sweet orange varieties.

*Texture*.—Firm.

*Surface texture*.—Relatively smooth.

*Color*.—Flavedo (epicarp): RHS 23A (yellow-orange). Albedo (mesocarp).—RHS 16C (yellow-orange). Stylar end: Closed.

*Oil cell density*.—176 to 180 oil cells per square centimeter.

*Oil gland size*.—Oil glands appear to be similarly distributed throughout most of the fruit flavedo, with interspersed large oil glands, and with small oil glands toward the fruit shoulder area; no pitting or pebbling is observed on the oil glands.

Flesh:

*Number of segments*.—9 to 10 segments per fruit on average.

*Segment walls*.—Soft, but of sufficient strength to maintain integrity as separated.

*Juice*.—Abundant.

*Color*.—Uniformly RHS 25B (orange).

*Texture*.—Soft.

*Vesicles*.—Medium thickness. Length: 14.2 to 14.4 mm on average. Width: 2.5 to 2.6 mm on average.

*Eating quality* (data from late April, 2008).—Sucrose content (average Brix): 13.7. Acidity (average): 0.85. Sugar acid ratio: 15.5.

Seeds:

*Type*.—Polyembryonic.

*Number*.—Ranges from 1 to 5, usually 4 to 5.

*Shape*.—Variable: clavate/club shaped to deltoid shaped.

*Size*.—Length: 2.5 to 4.5 mm on average. Width: 7.5 to 9 mm on average.

*Seed coat color*.—Outer Surface: RHS 155A (white) and slightly wrinkled. Inner surface: RHS 165C (greyed-orange).

*Cotyledon color*.—RHS 155A (white).

*Fruit parthenocarpy*.—High levels, similar to other commercial sweet oranges used in processing.

Resistance to disease: No obvious tree-debilitating disease problems have been observed in the trees or fruit currently grown, but systematic resistance testing has not been explored. Citrus canker lesions have been found on leaves and a few fruit of somaclone 'OLL-8', suggesting that its canker tolerance is less than that of 'Valencia', and probably more similar to that of 'Hamlin'.

What is claimed is:

1. A new and distinct cultivar of sweet orange tree as illustrated and described herein.

* * * * *